United States Patent [19]

Kirst

[11] 4,396,613
[45] Aug. 2, 1983

[54] 23-ESTER DERIVATIVES OF DMT AND METHOD OF USING SAME

[75] Inventor: Herbert A. Kirst, Indianapolis, Ind.

[73] Assignee: Eli Lilly and Company, Indianapolis, Ind.

[21] Appl. No.: 330,294

[22] Filed: Dec. 14, 1981

[51] Int. Cl.$^3$ .................. A61K 31/71; C07H 17/08
[52] U.S. Cl. ............................ 424/180; 536/7.1
[58] Field of Search ............... 536/17 R, 17 C, 7.1; 424/180

[56] References Cited

U.S. PATENT DOCUMENTS

| 3,459,853 | 8/1969 | Gorman et al. | 424/121 |
|---|---|---|---|
| 4,092,473 | 5/1978 | Okamoto et al. | 536/17 |
| 4,205,163 | 5/1980 | Mori et al. | 536/17 |
| 4,321,361 | 3/1982 | Baltz et al. | 536/17 R |

FOREIGN PATENT DOCUMENTS 33433 8/1981 European Pat. Off. .

OTHER PUBLICATIONS

Derwent Abstract 66634C/38 of Japanese Kokai J5 5043-013, Mar. 26, 1980, (Sanraku Ocean).
A. A. Nagel et al., "Selective Cleavage of the Mycinose Sugar from the Macrolide Antibiotic Tylosin: A Unique Glycosidic Scission," *J. Org. Chem.* 44 (12), 2050–2052 (1979).
A. Tanaka et al., "Synthesis of Recyclized Macrolide Antibiotics and Related Derivatives from Mycaminosyl Tylonolide", *Bull. Soc. Chem. Soc. Japan* 54, 3837–3845 (1981).
A. Tanaka et al., "Synthesis of 4'-Deoxymycaminosyl Tylonolide", *J. Antibiotics* 34, 1374–1376 (1981).
A. Tanaka et al., "Syntheses of Derivatives of 4'-Deoxymycaminosyl Tylonolide and Mycaminosyl Tylonolide Modified at C–23", *J. Antibiotics* 34, 1377–1380, (1981).
S. Omura, Derwent Abstract 82541D/45 of Japanese Kokai J56122–397, Sep. 25, 1981.

*Primary Examiner*—Johnnie R. Brown
*Attorney, Agent, or Firm*—Nancy J. Harrison; Arthur R. Whale

[57] ABSTRACT

23-Ester derivatives of demycinosyltylosin (DMT) of the formula:

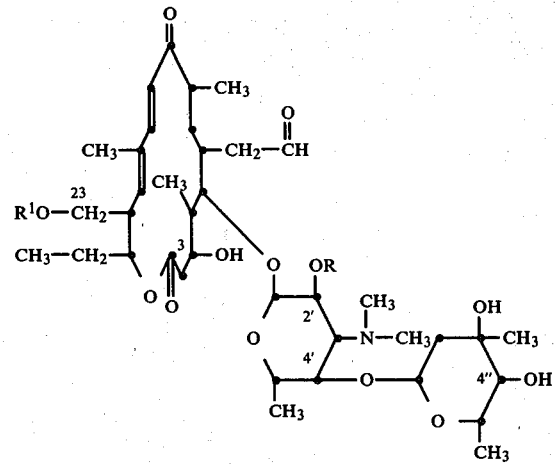

wherein R is selected from hydrogen, optionally substituted $C_1$–$C_5$-alkanoyl or optionally substituted benzoyl, phenylacetyl, or phenylpropionyl; and $R^1$ is an acyl group selected from:

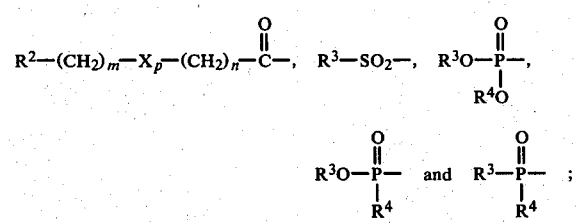

p is 0 or 1; m and n are integers from 0 to 4; $R^2$ is hydrogen, halo, $C_1$–$C_4$-alkyl, $C_3$–$C_8$-cycloalkyl, phenyl, $C_5$–$C_8$-cycloalkenyl, naphthyl, indenyl, tetralinyl, decalinyl, adamantyl, cinnoxacinyl, a monocyclic heterocyclic ring system comprising 3 to 8 atoms or a bicyclic heterocyclic ring system comprising 6 to 11 atoms, provided that at least 1 atom of the ring system is carbon and at least 1 atom of the ring system is a heteroatom selected from O, N, and S; and wherein $R^2$ and the connecting alkyl groups —$(CH_2)_m$— and —$(CH_2)_n$— are optionally substituted by one or two halo, methyl, ethyl, methoxy, amino, N-protected-amino, methylamino, dimethylamino, nitro, acetoxy, acetamido, azido, carbomethoxy, carboxamido, cyano, or hydroxyl groups, provided that, if the substituent is other than halo or alkyl, there can be no more than one substituent on any connecting —$CH_2$— group; X is O, S, —NH—, —N($CH_3$)—, —C≡C—, —CH=CH—, —C($CH_3$)=CH—, —CH=C($CH_3$)— or —C($CH_3$)=C($CH_3$)—; $R^3$ and $R^4$ are $C_1$–$C_5$-alkyl or optionally substituted phenyl or benzyl; and salts thereof are useful antibiotics or intermediates to antibiotics.

42 Claims, No Drawings

23-ESTER DERIVATIVES OF DMT AND METHOD OF USING SAME

SUMMARY OF THE INVENTION

This invention relates to 23-ester derivatives of demycinosyltylosin (DMT) having formula 1:

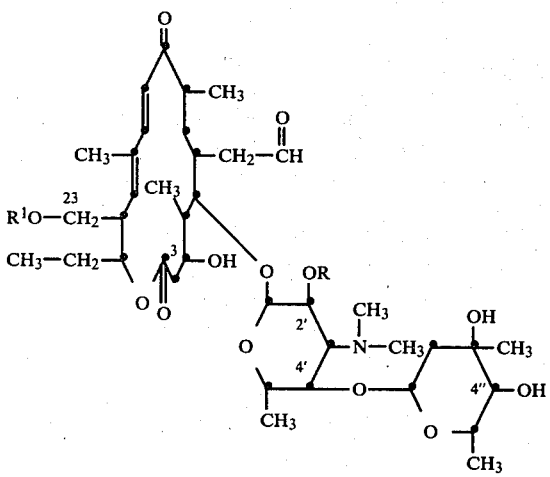

wherein R is hydrogen, optionally substituted $C_1$-$C_5$-alkanoyl or optionally substituted benzoyl, phenylacetyl, or phenylpropionyl; and $R^1$ is a specified acyl group, and to the acid addition salts of these compounds. The compounds of this invention are useful as antibiotics and/or as intermediates to antibiotics. This invention also relates to pharmaceutical compositions comprising these compounds and to methods of treatment wherein these compounds or compositions are administered to obtain an antibiotic effect or to enhance growth promotion in animals.

DETAILED DESCRIPTION OF THE INVENTION

This invention relates to new antibiotics. In particular, this invention relates to 23-ester derivatives of DMT and to their acid addition salts. This invention also relates to methods of treating certain infections with, methods of promoting growth in animals with, and pharmaceutical compositions comprising the specified ester derivatives of DMT and their pharmaceutically acceptable acid addition salts.

New, improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer body half life, and more advantageous rate or route of excretion and rate or pattern of metabolism) are some of the goals for improved antibiotics.

DMT is an antibiotic described by Richard H. Baltz, Gene M. Wild, and Eugene T. Seno in their copending application entitled DEMYCINOSYLTYLOSIN AND PROCESS FOR ITS PRODUCTION, Ser. No. 156,854, filed June 12, 1980. The structure of DMT is shown in formula 2:

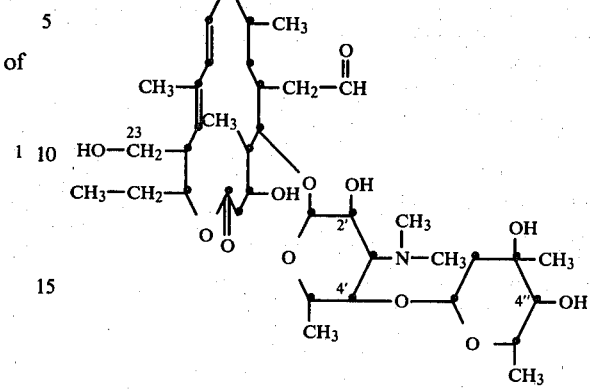

Esterification of the 23-hydroxyl group of macrolide antibiotics has not previously been reported because few macrolides have a free hydroxyl group at this position. Surprisingly, the 23-ester derivatives of DMT of this invention often have improved potency over DMT itself.

The ester derivatives of DMT of this invention are compounds of formula 1 wherein R is selected from hydrogen, optionally substituted $C_1$-$C_5$-alkanoyl or optionally substituted benzoyl, phenylacetyl, or phenylpropionyl; and $R^1$ is an acyl group selected from:

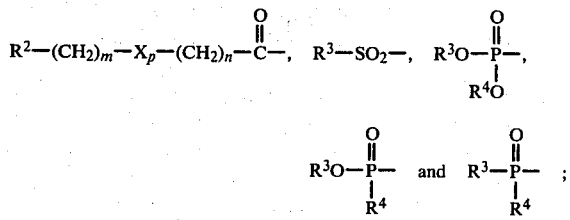

p is 0 or 1; m and n are integers from 0 to 4; $R^2$ is hydrogen, halo, $C_1$-$C_4$-alkyl, $C_3$-$C_8$-cycloalkyl, phenyl, $C_5$-$C_8$-cycloalkenyl, naphthyl, indenyl, tetralinyl, decalinyl, adamantyl, 1-ethyl-1,4-dihydro-4-oxo[1,3]dioxolo[4,5-g]cinnolin-3-yl(cinnoxacinyl), a monocyclic heterocyclic ring system comprising 3 to 8 atoms or a bicyclic heterocyclic ring system comprising 6 to 11 atoms, provided that at least 1 atom of the ring system is carbon and at least 1 atom of the ring system is a heteroatom selected from O, N, and S; and wherein $R^2$ and the connecting alkyl groups —$(CH_2)_m$— and —$(CH_2)_n$— are optionally substituted by one or two halo, methyl, ethyl, methoxy, amino, N-protected-amino, methylamino, dimethylamino, nitro, acetoxy, acetamido, azido, carbomethoxy, carboxamido, cyano, or hydroxyl groups, provided that, if the substituent is other than halo or alkyl, there can be no more than one substituent on any connecting —$CH_2$— group; X is O, S, —NH—, —N($CH_3$)—, —C≡C—, —CH═CH—, —C($CH_3$)═CH—, —CH═C($CH_3$)— or —C($CH_3$)═C($CH_3$)—; $R^3$ and $R^4$ are $C_1$-$C_5$-alkyl or optionally substituted phenyl or benzyl. The acid addition salts of these compounds are also part of this invention.

The term "optionally substituted $C_1$-$C_5$-alkanoyl" as used herein means an acyl moiety derived from a carboxylic acid containing from one to five carbon atoms. In such a moiety, the alkyl group can be straight, branched, or cyclic and can optionally bear one to three halo substituents. Halo substituents are selected from the group consisting of Cl, Br and F. Acetyl, chloroacetyl, trichloroacetyl, trifluoroacetyl, propionyl, n-butyryl, isobutyryl, n-valeryl, and isovaleryl are examples of such groups.

The terms "optionally substituted benzoyl, phenylacetyl or phenylpropionyl" and "optionally substituted phenyl or benzyl" mean that the phenyl portion of the moiety is optionally substituted by from one to five halo or methyl or by from one to two methoxyl, nitro or hydroxyl groups.

The terms "$C_1$–$C_4$-alkyl" and "$C_1$–$C_5$-alkyl" as used herein mean a straight- or branched-chain alkyl group containing from one to four or from one to five carbon atoms, respectively. Such groups include methyl, ethyl, isopropyl, n-butyl, sec-butyl, isobutyl and tert-butyl and, for the latter, n-pentyl and isovaleryl, and the like.

The term "$C_3$–$C_8$-cycloalkyl" means a saturated ring having from three to eight carbon atoms in the ring. Examples of such rings are cyclopropyl, cyclobutyl, cyclopentyl, cyclohexyl, and cyclooctyl. By "$C_5$–$C_8$-cycloalkenyl" is meant a carbocyclic ring which contains from five to eight carbon atoms and which also contains one or two double bonds. Cyclohexadienyl, cyclohexenyl, cyclopentenyl, and cyclooctadienyl are examples of such rings.

The term "monocyclic or bicyclic heterocyclic ring system" as used herein includes saturated or unsaturated heterocyclic moieties containing at least one carbon atom and at least one heteroatom selected from oxygen, nitrogen and sulfur. Heterocyclic groups contemplated include:

unsaturated 3 to 8-membered monocyclic groups, for example, pyrrolyl, $\Delta^3$-pyrrolinyl, imidazolyl, pyrazolyl, pyridyl, pyrimidyl, pyrazinyl, pyridazinyl, triazinyl, triazolyl (e.g., 4H-1,2,4-triazolyl, 1H-1,2,3-triazolyl, etc.), tetrazolyl (e.g., 1H-tetrazolyl, 2H-tetrazolyl, etc.), oxazolyl, isoxazolyl, oxadiazolyl (e.g., 1,2,4-oxadiazolyl, 1,3,4-oxadiazolyl, 1,2,5-oxadiazolyl, etc.), thiazolyl, isothiazolyl, thiadiazolyl (e.g., 1,2,4-thiadiazolyl, 1,3,4-thiadiazolyl, 1,2,5-thiadiazolyl, etc.), thienyl, furanyl, etc;

saturated 3 to 8-membered monocyclic groups, for example, pyrrolidinyl, imidazolidinyl, piperidinyl, piperazinyl, morpholinyl, thiazolidinyl, tetrahydrofuranyl, tetrahydrothienyl, tetrahydropyranyl, dioxanyl, etc.;

unsaturated 6 to 11-membered bicyclic groups, for example, indolyl, isoindolyl, coumaronyl, benzothiofuranyl, benzimidazolyl, quinolyl, isoquinolyl, benzopyrazolyl, cinnolinyl, quinazolinyl, benzoxazolyl, benzothiazolyl, benzoxazinyl, coumarinyl, etc.; and the like.

"N-protected-amino" means that the amino group is substituted by a suitable protecting group. Such a group must be one which is compatible with the other functional groups in DMT and which can be readily removed from the 23-O-acylated derivative.

When $R^1$ is an acyl group wherein X is —CH=CH—, —C(CH$_3$)$_2$=CH—, —CH=C(CH$_3$)— or —C(CH$_3$)=C(CH$_3$)—, the substituents on the double bond can be in either the cis or trans configuration.

Illustrative $R^1$ groups include those wherein:
(1) $R^1$ is

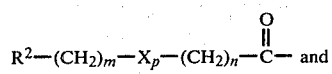

(a) $R^2$ is hydrogen or $C_1$–$C_4$-alkyl;
(b) p is 0;
(c) $R^2$ is optionally substituted phenyl;
(d) X is oxygen or —NH— and n is 0; or
(e) X is oxygen or sulfur and n is 1; and
(2) $R^1$ is $R^3$—SO$_2$ and
(a) $R^3$ is $C_1$–$C_5$-alkyl; or
(b) $R^3$ is optionally substituted phenyl.

The 23-ester derivatives of this invention are prepared from DMT or from 2'-0-ester derivatives of DMT. The preparation of DMT and of 2'-0-ester derivatives of DMT is described by Baltz et al. in application Ser. No. 156,854, which is incorporated herein by reference. The 2',23-diester compounds of this invention, i.e., compounds of formula 1 wherein R is other than hydrogen, can be prepared by esterifying DMT on the 2' and 23-hydroxyl groups or by esterifying a 2'-ester of DMT on the 23-hydroxyl group by treatment with acylating agents using conventional methods. The 23-monoester compounds of this invention, i.e., compounds of formula 1 wherein R is hydrogen, can be prepared by selectively de-esterifying 2',23-diester compounds.

In the absence of external base, esterification of the 2'-hydroxyl group of DMT is more facile than esterification of the 23-hydroxyl groups. Typical acylating agents include anhydrides, acyl halides (usually in combination with an acid scavenger), and active esters of organic acids. Acylation can also be achieved by using a mixture of an organic acid and a dehydrating agent such as N,N'-dicyclohexylcarbodiimide. Once formed, the desired ester derivatives can be separated and purified by known techniques.

A preferred method for the preparation of the symmetrical 2',23-diester derivatives of DMT, i.e., compounds of formula 1 wherein R and $R^1$ are identical and are other than hydrogen, comprises treating DMT in a basic solvent such as pyridine with a stoichiometric quantity (or a slight excess) of an acylating agent, such as an acyl anhydride, at about 0° C. to about room temperature for from about 1 to about 24 hours until esterification of the 2' and 23 hydroxyl groups is substantially complete. The 2',23-diester derivatives can be isolated from the reaction mixture by standard procedures such as extraction, chromatography and crystallization.

In an analogous manner, the unsymmetrical 2',23-diester derivatives of DMT, i.e., compounds of formula 1 wherein R and $R^1$ are different, can be prepared by acylation of the appropriate 2'-monoesters of DMT.

The 23-monoester derivatives of DMT can be prepared from the corresponding 2',23-diester derivatives of DMT by removing the acyl group from the 2'-position. This selective de-esterification can be accomplished using known procedures, such as warming or refluxing in aqueous methanol. The de-esterification reaction can be monitored using standard techniques, such as thin-layer chromatography (TLC), to determine the time required for removal of the 2'-acyl group.

23-Monoester derivatives of DMT can also be prepared directly from DMT as described in my copending application with John Toth entitled METHOD OF PREPARING 23-MONOESTERS OF OMT AND DMT, Ser. No. 330,295, filed Dec. 14, 1981. This method comprises carrying out the esterification of DMT at low to room temperatures with an appropriately selected acylating agent such as an acyl chloride in the presence of an external base such as pyridine or 2,4,6-collidine until acylation of the 23-hydroxyl group is substantially complete. The product is isolated using standard procedures.

The DMT ester derivatives of this invention form acid addition salts. These acid addition salts are also useful as antibiotics and are a part of this invention. In another aspect, such salts are useful as intermediates, for example, for separating and purifying the DMT ester derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

Pharmaceutically acceptable acid addition salts are an especially preferred group of salts of this invention.

DMT can be prepared by fermentation of *Streptomyces fradiae* NRRL 12170 under submerged aerobic conditions until a substantial level of antibiotic activity is produced. DMT can be extracted from basified broth filtrate with organic solvents such as ethyl acetate and can be further purified by extraction, chromatography, and/or crystallization. The DMT-producing strain of *Streptomyces fradiae* has been deposited and made part of the stock culture collection of the Northern Regional Research Center, Agricultural Research, North Central Region, 1815 North University St., Peoria, Ill., 61604, from which it is available to the public under the accession number NRRL 12170.

Illustrative DMT esters of this invention include those compounds of formula 1 listed in Table I.

TABLE I

| Illustrative 23-Ester Derivatives of DMT | | |
|---|---|---|
| Compound No. | R | $R^1$ |
| 1 | acetyl | acetyl |
| 2 | H | acetyl |
| 3 | propionyl | propionyl |
| 4 | H | propionyl |
| 5 | acetyl | propionyl |
| 6 | propionyl | acetyl |
| 7 | acetyl | n-octanoyl |
| 8 | acetyl | pivaloyl |
| 9 | acetyl | phenylacetyl |
| 10 | H | phenylacetyl |
| 11 | acetyl | cinnamoyl |
| 12 | acetyl | phenoxyacetyl |
| 13 | acetyl | phenylpropionyl |
| 14 | acetyl | p-chlorophenylacetyl |
| 15 | acetyl | p-nitrophenylacetyl |
| 16 | acetyl | trichloroacetyl |
| 17 | phenylacetyl | phenylacetyl |
| 18 | acetyl | phenyl-n-valeryl |
| 19 | acetyl | naphthoyl |
| 20 | acetyl | 2,5-dimethoxyphenylacetyl |
| 21 | acetyl | 1H—imidazol-1-ylcarbonyl |
| 22 | H | 1H—imidazol-1-ylcarbonyl |
| 23 | acetyl | adamantanoyl |
| 24 | acetyl | methoxycarbonyl |
| 25 | H | methoxycarbonyl |
| 25 | H | methoxycarbonyl |
| 26 | H | [(3-hydroxy-n-propyl)-amino]carbonyl |
| 27 | H | [(8-amino-n-octyl)amino]-carbonyl |
| 28 | H | (4-hydroxy-1-piperidinyl)-carbonyl |
| 29 | H | [[2-(4-morpholinyl)ethyl]-amino]carbonyl |
| 30 | acetyl | benzylaminocarbonyl |

The DMT 23-ester derivatives of this invention inhibit the growth of pathogenic bacteria, especially gram-positive bacteria, Mycoplasma species and Pasteurella species. For example, Tables II and III show the minimal inhibitory concentrations (MIC's) at which illustrative compounds inhibit certain bacteria. The MIC's in Table II were determined by standard agar-dilution assays. The MIC's in Table III were obtained using a conventional broth-dilution microtiter test.

TABLE II

| Antibiotic Activity of DMT Ester Derivatives | | | | | |
|---|---|---|---|---|---|
| Test Organism | Test Compound[a] | | | | |
| | 1 | 3 | 4 | 5 | 6 |
| *Staphylococcus aureus* X1.1 | 1 | 0.5 | 1 | 0.5 | 0.5 |
| *Staphylococcus aureus* V41[b] | 1 | 0.5 | 0.5 | 0.5 | 0.5 |
| *Staphylococcus aureus* X400[c] | 2 | 2 | 2 | 1 | 2 |
| *Staphylococcus aureus* S13E | 2 | 1 | 1 | 1 | 1 |
| *Staphylococcus epidermidis* EPI1 | 2 | 0.5 | 1 | 1 | 1 |
| *Staphylococcus epidermidis* EPI2 | 2 | 1 | 1 | 1 | 1 |
| *Streptococcus pyogenes* C203 | 1 | 0.5 | 0.5 | 0.5 | 0.5 |
| *Streptococcus pneumoniae* Park I | 0.25 | 0.5 | 0.125 | 0.5 | 0.125 |
| Streptococcus Group D X66 | 2 | 1 | 1 | 1 | 1 |
| Streptococcus Group 9960 | 1 | 1 | 1 | 1 | 1 |
| *Haemophilus influenzae* Holt[d] | 16 | 16 | 32 | 16 | 16 |
| *Haemophilus influenzae* R252[e] | 16 | 16 | 32 | 32 | 16 |
| | 7 | 8 | 9 | 10 | 11 |
| *Staphylococcus aureus* X1.1 | 2 | 0.5 | 0.5 | 0.25 | 1 |
| *Staphylococcus aureus* V41[b] | 2 | 0.5 | 0.5 | 0.5 | 0.5 |
| *Staphylococcus aureus* X400[c] | 4 | 1 | 0.5 | 0.5 | 2 |
| *Staphylococcus aureus* S13E | 2 | 0.5 | 0.5 | 0.25 | 1 |
| *Staphylococcus epidermidis* EPI1 | 2 | 0.5 | 0.5 | 0.5 | 1 |
| *Staphylococcus epidermidis* EPI2 | 4 | 1 | 0.5 | 0.5 | 4 |
| *Streptococcus pyogenes* C203 | 0.5 | 0.25 | 0.125 | 0.125 | 1 |
| *Streptococcus pneumoniae* Park I | 0.5 | 0.06 | 0.015 | 0.03 | 0.25 |
| Streptococcus Group D X66 | 2 | 0.5 | 0.5 | 0.5 | 2 |
| Streptococcus Group 9960 | 2 | 0.5 | 0.25 | 0.25 | 2 |
| *Haemophilus influenzae* Holt[d] | >128 | 16 | 4 | 2 | 128 |

TABLE II-continued
Antibiotic Activity of DMT Ester Derivatives

| Test Organism | Test Compound[a] | | | | |
|---|---|---|---|---|---|
| Haemophilus influenzae R252[e] | >128 | 4 | 4 | 2 | 128 |

| | 12 | 13 | 14 | 15 | 16 |
|---|---|---|---|---|---|
| Staphylococcus aureus X1.1 | 0.25 | 0.25 | 0.5 | 0.25 | 1 |
| Staphylococcus aureus V41[b] | 0.25 | 1 | 2 | 0.5 | 2 |
| Staphylococcus aureus X400[c] | 0.5 | 1 | 2 | 0.5 | 4 |
| Staphylococcus aureus S13E | 0.5 | 0.5 | 1 | 0.25 | 1 |
| Staphylococcus epidermidis EPI1 | 0.5 | 1 | 1 | 0.5 | 1 |
| Staphylococcus epidermidis EPI2 | 0.5 | 1 | 2 | 0.5 | 4 |
| Streptococcus pyogenes C203 | 0.125 | 0.25 | 0.5 | 0.125 | 0.5 |
| Streptococcus pneumoniae Park I | 0.06 | 0.015 | 0.06 | 0.03 | 0.03 |
| Streptococcus Group D X66 | 0.5 | 0.5 | 1 | 0.25 | 1 |
| Streptococcus Group 9960 | 0.5 | 0.5 | 1 | 0.25 | 1 |
| Haemophilus influenzae Holt[d] | 16 | 2 | 4 | 8 | 2 |
| Haemophilus influenzae R252[e] | 8 | 2 | 4 | 4 | 2 |

| | 17 | 18 | 19 | 20 | 21 |
|---|---|---|---|---|---|
| Staphylococcus aureus X1.1 | 1 | 1 | 1 | 0.5 | 1 |
| Staphylococcus aureus V41[b] | 1 | 2 | 2 | 0.5 | 2 |
| Staphylococcus aureus X400[c] | 2 | 2 | 2 | 0.5 | 2 |
| Staphylococcus aureus S13E | 1 | 1 | 1 | 0.5 | 1 |
| Staphylococcus epidermidis EPI1 | 1 | 1 | 2 | 0.5 | 2 |
| Staphylococcus epidermidis EPI2 | 1 | 2 | 2 | 0.5 | 2 |
| Streptococcus pyogenes C203 | 0.5 | 0.5 | 0.5 | 0.25 | 0.5 |
| Streptococcus pneumoniae Park I | 0.125 | 0.125 | 0.25 | 0.06 | 0.125 |
| Streptococcus Group D X66 | 1 | 2 | 2 | 0.5 | 2 |
| Streptococcus Group 9960 | 1 | 1 | 1 | 2 | 1 |
| Haemophilus influenzae Holt[d] | >128 | >128 | >128 | 32 | 16 |
| Haemophilus influenzae R252[e] | >128 | >128 | >128 | 16 | 8 |

| | 22 | 23 | 24 | 25 | 26 |
|---|---|---|---|---|---|
| Staphylococcus aureus X1.1 | 0.5 | 2 | 0.5 | 0.25 | 1 |
| Staphylococcus aureus V41[b] | 1 | 2 | 0.5 | 0.5 | 2 |
| Staphylococcus aureus X400[c] | 1 | 2 | 0.5 | 0.5 | 4 |
| Staphylococcus aureus S13E | 0.5 | 2 | 0.5 | 0.25 | 4 |
| Staphylococcus epidermidis EPI1 | 0.5 | 2 | 0.5 | 0.5 | 1 |
| Staphylococcus epidermidis EPI2 | 0.5 | 4 | 0.5 | NT[f] | 2 |
| Streptococcus pyogenes C203 | 0.25 | 2 | 0.25 | 0.25 | 0.25 |
| Streptococcus pneumoniae Park I | NT | 1 | 0.06 | 0.06 | 0.125 |
| Streptococcus Group D X66 | 1 | 4 | 0.5 | 0.5 | 2 |
| Streptococcus Group 9960 | 0.5 | 4 | 0.5 | 0.5 | 2 |
| Haemophilus influenzae Holt[d] | 16 | >128 | 16 | 8 | 16 |
| Haemophilus influenzae R252[e] | 8 | >128 | 8 | 8 | NT |

| | 27 | 28 | 29 | 30 |
|---|---|---|---|---|
| Staphylococcus aureus X1.1 | 2 | 1 | 1 | 0.5 |
| Staphylococcus aureus V41[b] | 2 | 1 | 1 | 1 |
| Staphylococcus aureus X400[c] | 8 | 2 | 4 | 0.5 |
| Staphylococcus aureus S13E | 4 | 2 | 2 | 0.5 |
| Staphylococcus epidermidis EPI1 | 2 | 0.5 | 1 | 0.5 |
| Staphylococcus epidermidis EPI2 | 4 | 2 | 2 | 0.5 |
| Streptococcus pyogenes C203 | 1 | 0.25 | 0.5 | 0.5 |
| Streptococcus pneumoniae Park I | 0.25 | 0.125 | 0.125 | NT |
| Streptococcus Group D X66 | 4 | 1 | 2 | 0.5 |
| Streptococcus Group 9960 | 4 | 1 | 2 | 0.5 |
| Haemophilus influenzae Holt[d] | 32 | 8 | 16 | 8 |
| Haemophilus influenzae R252[e] | 32 | 16 | 16 | 4 |

[a]Compound numbers from Table I
[b]Penicillin-resistant strain
[c]Methicillin-resistant-strain
[d]Ampicillin-sensitive strain
[e]Ampicillin-resistant strain
[f]NT = not tested

TABLE III
Antibiotic Activity of DMT Ester Derivatives

| Test Organism | Test Compound[a] | | | | |
|---|---|---|---|---|---|
| | 1 | 3 | 4 | 5 | 6 |
| Staphylococcus aureus | 0.78 | 0.78 | 0.78 | 1.56 | 0.78 |
| Streptococcus sp. 80 | 0.78 | 0.78 | 0.39 | ≦0.78 | 0.39 |
| Pasteurella multocida 17E[b] | 6.25 | 6.25 | 6.25 | 6.25 | 6.25 |
| Pasteurella multocida 60A[c] | 12.5 | 12.5 | 25 | 12.5 | 12.5 |
| Mycoplasma gallisepticum | 0.39 | 0.78 | 0.39 | ≦0.024 | 0.39 |
| Mycoplasma synoviae | NT[d] | 0.195 | NT | 0.097 | 0.195 |
| Mycoplasma hyorhinis | 3.12 | 1.56 | 3.12 | 1.56 | 0.78 |

| | 7 | 8 | 9 | 10 | 11 |
|---|---|---|---|---|---|
| Staphylococcus aureus | 1.56 | 3.12 | 0.195 | 0.78 | 1.56 |
| Streptococcus sp. 80 | 1.56 | >0.78 | ≦0.048 | 0.097 | 0.78 |
| Pasteurella multocida 17E[b] | >50 | 12.5 | 3.12 | 1.56 | 12.5 |
| Pasteurella multocida 60A[c] | >50 | 12.5 | 6.25 | 3.12 | >50 |
| Mycoplasma gallisepticum | 1.56 | 0.39 | ≦0.048 | ≦0.048 | 0.39 |
| Mycoplasma synoviae | 12.5 | 0.39 | NT | ≦0.048 | 3.12 |
| Mycoplasma hyorhinis | 6.25 | 3.12 | 0.78 | 1.56 | 6.25 |

| | 12 | 13 | 14 | 15 | 16 |
|---|---|---|---|---|---|
| Staphylococcus aureus | 0.39 | 0.78 | 0.39 | 1.56 | 1.56 |

TABLE III-continued

Antibiotic Activity of DMT Ester Derivatives

| Test Organism | Test Compound[a] | | | | |
|---|---|---|---|---|---|
| Streptococcus sp. 80 | 0.195 | ≦0.048 | 0.78 | 0.39 | 0.39 |
| Pasteurella multocida 17E[b] | 6.25 | 1.56 | 3.12 | 3.12 | 6.25 |
| Pasteurella multocida 60A[c] | 6.25 | 12.5 | 6.25 | 6.25 | 12.5 |
| Mycoplasma gallisepticum | 0.097 | ≦0.048 | <0.048 | 0.39 | 0.39 |
| Mycoplasma synoviae | 0.78 | NT | 0.78 | <0.05 | NT |
| Mycoplasma hyorhinis | 6.25 | 3.12 | 6.25 | 0.78 | 3.12 |
| | 17 | 18 | 19 | 20 | 21 |
| Staphylococcus aureus | 0.78 | 1.56 | 1.56 | 0.78 | 6.25 |
| Streptococcus sp. 80 | 0.78 | 0.78 | 1.56 | 0.195 | 0.78 |
| Pasteurella multocida 17E[b] | 6.25 | 50 | >50 | 12.5 | 12.5 |
| Pasteurella multocida 60A[c] | 25 | >50 | 50 | 25 | 12.5 |
| Mycoplasma gallisepticum | 0.78 | <0.05 | 1.56 | 0.195 | 0.78 |
| Mycoplasma synoviae | 1.56 | 6.25 | 6.25 | 0.39 | 0.78 |
| Mycoplasma hyorhinis | 6.25 | 12.5 | 25 | 1.56 | 1.56 |
| | 22 | 23 | 24 | 25 | 26 |
| Staphylococcus aureus | 6.25 | 6.25 | 3.12 | 1.56 | 1.56 |
| Streptococcus sp. 80 | 1.56 | <0.78 | 0.78 | 0.78 | 0.39 |
| Pasteurella multocida 17E[b] | 12.5 | 50 | 6.25 | 6.25 | 6.25 |
| Pasteurella multocida 60A[c] | 25 | >50 | 12.5 | 12.5 | 12.5 |
| Mycoplasma gallisepticum | 3.12 | 6.25 | 0.78 | 0.097 | 0.78 |
| Mycoplasma synoviae | 1.56 | 1.56 | 0.78 | 0.097 | 0.39 |
| Mycoplasma hyorhinis | 1.56 | 25 | 1.56 | 1.56 | 6.25 |
| | 27 | 28 | 29 | 30 | |
| Staphylococcus aureus | 6.25 | 1.56 | 1.56 | 1.56 | |
| Streptococcus sp. 80 | 0.78 | 0.39 | 0.78 | 0.78 | |
| Pasteurella multocida 17E[b] | 25 | 12.5 | 12.5 | 12.5 | |
| Pasteurella multocida 60A[c] | 50 | 25 | 25 | 12.5 | |
| Mycoplasma gallisepticum | 0.78 | 0.39 | 0.39 | 0.39 | |
| Mycoplasma synoviae | 3.12 | 0.78 | 1.56 | 0.78 | |
| Mycoplasma hyorhinis | 3.12 | 0.78 | 6.25 | 1.56 | |

[a] Compound numbers from Table I.
[b] Bovine isolate.
[c] Avian isolate.
[d] NT = not tested.

The 23-ester derivatives of DMT of this invention have shown in vivo antimicrobial activity against experimental bacterial infections caused by gram-positive bacteria. When two doses of test compound were admininstered to mice with experimental infections, the activity observed was measured as an $ED_{50}$ value [effective dose in mg/kg to protect 50% of the test animals: see Warren Wick, et al., *J. Bacteriol.* 81, 233–235 (1961)]. $ED_{50}$ values observed for illustrative compounds are given in Table IV.

TABLE IV $ED_{50}$ Values of 23-Esters of DMT[a]

| | Streptococcus pyogenes C203 | |
|---|---|---|
| Test Compound[b] | Subcutaneous | Oral |
| 1 | >20 | 212 |
| 3 | >20 | 117 |
| 4 | 13 | 300 |
| 25 | 7.6 | >100 |

[a] mg/kg × 2; doses given 1 and 4 hours post-infection
[b] Compound numbers from Table I This invention also relates to methods of controlling gram-positive infections. In carrying out the methods of this invention, an effective amount of a compound of formula 1 is administered parenterally to an infected or susceptible warm-blooded animal. The dose which is effective to control gram-positive infections will vary with the severity of the infection and the age, weight, and condition of the animal. The total dose required for protection will generally, however, be in the range of from about 1 to about 100 mg/kg and preferably will be in the range of from about 5 to about 50 mg/kg. Suitable dosage regimens can be constructed.

In another aspect, this invention relates to compositions useful for the control of gram-positive infections. These compositions comprise a compound of formula 1 together with a suitable pharmaceutical vehicle. Such compositions may be formulated for parenteral administration by methods recognized in the pharmaceutical art. Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions employ a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necesssary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which effect the hydrophilicity, density, and surface tension of the liquid suspending medium can assist in making injectable suspensions in individual cases. For example, silicone antifoams, sorbitol, and sugars can be useful suspending agents.

In order to illustrate more fully the operation of this invention, the following examples are provided:

PREPARATION 1

Preparation of DMT

A. Shake-flask Fermentation of DMT

A lyophilized pellet of *Streptomyces fradiae* NRRL 12170 is dispersed in 1–2 ml of sterilized water. A portion of this solution (0.5 ml) is used to inoculate a vegetative medium (150 ml) having the following composition:

| Ingredient | Amount (%) |
|---|---|
| Corn steep liquor | 1.0 |
| Yeast extract | 0.5 |
| Soybean grits | 0.5 |
| CaCO$_3$ | 0.3 |
| Soybean oil (crude) | 0.45 |
| Deionized water | 97.25 |

Alternatively, a vegetative culture of *S. fradiae* NRRL 12170, preserved in 1-ml volumes in liquid nitrogen, is rapidly thawed and used to inoculate the vegetative medium. The inoculated vegetative medium is incubated in a 500-ml Erlenmeyer flask at 29° C. for about 48 hours on a closed-box shaker at 300 rpm.

This incubated vegetative medium (0.5 ml) is used to inoculate 7 ml of a production medium having the following composition:

| Ingredient | Amount (%) |
| --- | --- |
| Beet molasses | 2.0 |
| Corn meal | 1.5 |
| Fish meal | 0.9 |
| Corn gluten | 0.9 |
| NaCl | 0.1 |
| $(NH_4)_2HPO_4$ | 0.04 |
| $CaCO_3$ | 0.2 |
| Soybean oil (crude) | 3.0 |
| Deionized water | 91.36 |

The inoculated fermentation medium is incubated in a 50-ml bottle at 29° C. for about 6 days on a closed-box shaker at 300 rpm.

B. Tank Fermentation of DMT

In order to provide a larger volume of inoculum, 1200 ml of incubated vegetative medium, prepared in a manner similar to that described in section A, is used to inoculate 250 gallons of a second-stage vegetative growth medium having the following composition:

| Ingredient | Amount (%) |
| --- | --- |
| Corn steep liquor | 1.0 |
| Soybean oil meal | 0.5 |
| Yeast extract | 0.5 |
| $CaCO_3$ | 0.3 |
| Soybean oil (crude) | 0.5 |
| Lecithin (crude) | 0.015 |
| Water | 97.185 |
| Adjust pH to 8.5 with 50% NaOH solution. | |

This second-stage vegetative medium is incubated in a 350-gallon tank for about 48 hours at 28° C., with adequate aeration and agitation.

Incubated second-stage medium (144 gallons) thus prepared is used to inoculate 1000 gallons of sterile production medium having the following composition:

| Ingredient | Amount (%) |
| --- | --- |
| Fish meal | 0.875 |
| Corn meal | 1.5 |
| Corn gluten | 0.875 |
| $CaCO_3$ | 0.2 |
| NaCl | 0.1 |
| $(NH_4)_2HPO_4$ | 0.04 |
| Beet molasses | 2.0 |
| Soybean oil (crude) | 3.0 |
| Lecithin | 0.09 |
| Water | 91.32 |
| Adjust pH to 7.2 with 50% NaOH solution. | |

The inoculated production medium is allowed to ferment in a 1600-gallon tank for 8 to 9 days at a temperature of 28° C. The fermentation medium is aerated with sterile air to keep the dissolved oxygen level between about 30% and 50% and is stirred with conventional agitators at about 250 rpm.

C. Isolation of DMT

Harvested whole broth (3800 L), obtained as described in Section B, is filtered, using a filter aid. The mycelial cake is washed with water; this water wash is added to the filtrate.

The pH of the filtrate is adjusted to pH 9.2, using a 50% aqueous solution of sodium hydroxide (9.5 L). The filtrate is extracted with ethyl acetate (2000 L). Deionized water (450 L) and sodium phosphate monobasic (6.4 kg) are added to the ethyl acetate extract with thorough mixing. The pH of this mixture is adjusted from about pH 6.0 to pH 4.35, using a phosphoric acid solution (3300 ml; 2 parts water to one part phosphoric acid). The aqueous phase is separated. The pH of the enriched aqueous phase is adjusted to pH 6.5 using a 50% aqueous sodium hydroxide solution (700 ml).

The resulting solution is concentrated to a volume of about 225 L under vacuum. The pH of the concentrated solution is adjusted to pH 9.2 by the addition of 10% aqueous sodium hydroxide (16 L). The resulting basic solution is permitted to stand overnight. The crystals which form are separated by filtration, washed with deionized water (50 L), and dried to give about 8.6 kg of product. The product thus obtained can be recrystallized from acetone-water.

PREPARATION 2

2'-O-Acetyl-DMT

DMT (10 g, 13.5 mmol) was dissolved in acetone (260 ml) and treated with acetic anhydride (1.6 ml, 15.7 mmol) dropwise with stirring at room temperature. After stirring overnight (18 hours), the solvent was evaporated under reduced pressure. The residue thus obtained was dissolved in ethyl acetate (200 ml), and this solution was extracted with saturated $NaHCO_3$ solution (2×200 ml). The organic solution was dried ($Na_2SO_4$), filtered and evaporated. The residue was dissolved in a small volume of ethyl acetate, loaded on a silica gel column (Waters Prep 500) and eluted with ethyl acetate (4 liters). Fractions containing the desired product was identified by TLC, combined and evaporated to dryness, yielding 6.5 g (61%) of 2'-O-acetyl-DMT.

PREPARATION 3

2'-O-Propionyl-DMT

In a manner analogous to Preparation 2, DMT (6.0 g, 8.1 mmol) in acetone (120 ml) was treated with propionic anhydride (1.2 ml, 9.2 mmol). After workup and chromatography, 3.7 g (57%) of 2'-O-propionyl-DMT was isolated.

EXAMPLE 1

2',23-Di-O-Acetyl-DMT

DMT (3 g, 4.05 mmol) was dissolved in dichloromethane (90 ml) and pyridine (7.8 ml) and treated with acetic anhydride (1.4 ml, 13.7 mmol) dropwise with stirring at room temperature. After stirring overnight (17 hours), the solution was diluted with toluene (15 ml), and the solvent was evaporated under reduced pressure. The residue, dissolved in a small volume of ethyl acetate, was loaded on a silica gel column (Waters Prep 500) and was eluted with ethyl acetate (4 liters), yielding 2.1 g of crude product. This material, dissolved in a minimum volume of toluene, was loaded onto a flash-chromatography column of silica gel (300 ml). This was eluted sequentially with 3:1 toluene-ethyl acetate (300 ml), 5:4 toluene-ethyl acetate (600 ml), and 1:1 toluene-ethyl acetate (1000 ml). Fractions containing the desired product were located by TLC, combined and evaporated to dryness to yield 1.7 g (64%) of 2',23-di-O-acetyl-DMT.

EXAMPLE 2

2',23-Di-O-Propionyl-DMT

DMT (3 g, 4.05 mmole) was dissolved in dichloromethane (90 ml) and pyridine (7.8 ml) and treated with propionic anhydride (1.8 ml, 13.8 mmol) dropwise with stirring at room temperature. After the reaction was stirred overnight, toluene (15 ml) was added. The resulting solution was evaporated to dryness under reduced pressure. The residue, dissolved in toluene (20 ml), was loaded onto a flash-chromatography column of silica gel (E. Merck 60, 300 ml) which was eluted sequentially with 3:1 toluene-ethyl acetate (300 ml), 5:4 toluene-ethyl acetate (300 ml), and 1:1 toluene-ethyl acetate (1000 ml). Fractions were combined, based on TLC results, and evaporated to dryness to give 2.5 g (72%) of 2',23-di-O-propionyl-DMT.

EXAMPLE 3

2'-O-Acetyl-23-O-propionyl DMT

2'-O-Acetyl-DMT (6 g, 7.7 mmol) was dissolved in dichloromethane (180 ml) and pyridine (15 ml) and treated with propionic anhydride (1.2 ml, 9.2 mmol) dropwise with stirring at room temperature. After being stirred overnight (17 hours), the solution was diluted with toluene (300 ml) and evaporated to dryness under reduced pressure. The residue was dissolved in toluene, and this solution was extracted with saturated $NaHCO_3$ solution. The toluene layer was dried ($Na_2SO_4$), filtered and evaporated. The residue, dissolved in a small volume of toluene, was loaded onto a flash-chromatography column of silica gel (300 ml) packed in 1:1 toluene-ethyl acetate. The column was eluted with 1:1 toluene-ethyl acetate (1 liter). Fractions containing the desired product were identified by TLC, combined and evaporated under reduced pressure to yield 4.5 g (70%) of 2'-O-acetyl-23-O-propionyl-DMT.

EXAMPLE 4

23-O-Acetyl-2'-O-propionyl-DMT

Using conditions similar to those in Example 3, 2'-O-propionyl-DMT (1.5 g, 2 mmol) in dichloromethane (45 ml) and pyridine (3.9 ml) was treated with acetic anhydride (0.3 ml, 2.9 mmol). After chromatography on silica gel (Waters Prep 500), 0.81 g (51%) of 23-O-acetyl-2'-O-propionyl-DMT was isolated.

EXAMPLE 5

2'-O-Acetyl-23-O-phenylacetyl-DMT

2'-O-Acetyl-DMT (2.75 g. 3.5 mmol) was dissolved in dichloromethane (75 ml) and pyridine (0.8 ml) and treated with a solution of phenylacetyl chloride (0.56 ml, 3.5 mmol) in dichloromethane (13 ml) dropwise with stirring at room temperature. After 1.5 hours, additional phenylacetyl chloride (0.56 ml) in dichloromethane (13 ml) was added. After another 1.5 hours, starting material had been consumed (TLC analysis). The solution was then evaporated to dryness under reduced pressure; the residue was dissolved in dichloromethane; and this solution was extracted with saturated $NaHCO_3$ solution. The organic layer was dried ($Na_2SO_4$), filtered and evaporated to dryness. The residue was dissolved in toluene and chromatographed on a silica gel column (Waters Prep 500). Elution was conducted with a linear gradient of 1:1 toluene-ethyl acetate (4 liters) and ethyl acetate (4 liters). Fractions containing the desired product were located by TLC, combined and evaporated to yield 1.1 g (35%) of 2'-O-acetyl-23-O-phenylacetyl-DMT.

EXAMPLE 6

23-O-Propionyl-DMT

2'-O-Acetyl-23-O-propionyl-DMT (1.6 g, 1.9 mmol) was dissolved in 95% methanol (80 ml) and stirred at room temperature for 42 hours. The solution was evaporated to dryness under reduced pressure. The residue was dissolved in a small volume of toluene, loaded onto a flash-chromatography column of silica gel (E. Merck 60, 200 ml) and eluted with 1:1 toluene-ethyl acetate (2 liters). Fractions containing the desired product were identified by TLC, combined and evaporated under reduced pressure to yield 1.2 g (79%) of 23-O-propionyl-DMT.

EXAMPLE 7

23-O-Phenylacetyl-DMT

2'-O-Acetyl-23-O-phenylacetyl-DMT (0.6 g, 0.67 mmol) was dissolved in 80% aqueous methanol (50 ml), and this solution was gently refluxed for 4.5 hours. The solution was cooled to room temperature and evaporated to dryness under reduced pressure to yield 0.39 (68%) of 23-O-phenylacetyl-DMT.

EXAMPLE 8

2'-O-Acetyl-23-O-phenoxyacetyl-DMT

2'-O-Acetyl-DMT (2.75 g, 3.5 mmol) was dissolved in dichloromethane (75 ml) and pyridine (0.8 ml) and treated with a solution of phenoxyacetyl chloride (1.2 ml, 8.8 mmol) in dichloromethane (25 ml) dropwise with stirring at room temperature. After 1 hour, the reaction mixture was poured into saturated $NaHCO_3$ solution (200 ml). The organic layer was separated, dried ($Na_2SO_4$), filtered and evaporated under reduced pressure. The residual solid foam was loaded onto a flash-chromatography silica-gel column and eluted using 1:1 toluene-ethyl acetate. Based on TLC results, fractions were combined and evaporated to dryness to give 1.5 g of 2'-O-acetyl-23-O-phenoxyacetyl-DMT.

EXAMPLE 9

2'-O-Acetyl-23-O-(p-chlorophenylacetyl)-DMT p-Chlorophenylacetic acid (4.3 g, 25 mmol) and 1-hydroxybenzotriazole (3.4 g, 25 mmol) were dissolved in THF (150 ml). The solution was cooled in an ice bath and treated with N,N'-dicyclohexylcarbodiimide (5.2 g, 25.3 mmol). The reaction mixture was stirred at 0° C. for 3 hours and then placed in a refrigerator overnight. The mixture was filtered, and the filtrate was evaporated under reduced pressure. The residue was dissolved in acetone (75 ml), filtered and treated with 2'-O-acetyl-DMT (10 g, 12.8 mmol) and imidazole (0.87 g, 12.8 mmol). Acetone was added to give a solution volume of 125 ml, and then triethylamine (1.87 ml, 12.8 mmol) was added. After the reaction was stirred for 20 hours at room temperature, the solvent was evaporated under reduced pressure. The residue was loaded on a flash-chromatography silica-gel column which was eluted with a gradient of 4:1 toluene-ethyl acetate to ethyl acetate alone. The desired fractions were combined on the basis of TLC results and evaporated to dryness to give 4.75 g of 2'-O-acetyl-23-O-(p-chlorophenylacetyl)-DMT.

EXAMPLE 10

2'-O-Acetyl-23-O-(p-nitrophenylacetyl)-DMT

2'-O-Acetyl-DMT (4.0 g, 5.1 mmol) and p-nitrophenylacetic acid (1.4 g, 7.7 mmol) were dissolved in dichloromethane (50 ml) and treated with N,N'-dicyclohexylcarbodiimide (1.6 g, 7.7 mmol) and 4-dimethylaminopyridine (0.1 g). The reaction mixture was stirred at room temperature for 5 hours. The precipitate which formed was separated by filtration. The filtrate was evaporated to dryness under reduced pressure and the residue thus obtained was dissolved in ethyl acetate. Impurities were separated by filtration and the filtrate was evaporated again to dryness. The residue obtained was purified by flash chromatography on silica gel, eluting stepwise with mixtures of toluene-ethyl acetate (400 ml of 2:1, 600 ml of 1:1 and 600 ml of 1:2) and then with ethyl acetate (1 liter). Fractions containing the desired product were located by TLC, combined and evaporated to dryness to give 2.2 g of 2'-O-acetyl-23-O-(p-nitrophenylacetyl)-DMT.

EXAMPLE 11

Injectable Formulations (A) A formula 1 base is added to propylene glycol. Water and benzyl alcohol are added so that the solution contains 50% (by volume) propylene glycol, 4% (by volume) benzyl alcohol, and 200 mg/ml of a formula 1 base.

(B) A solution is prepared as described in Section A except that the solution contains 50 mg/ml of a formula 1 base.

(C) A solution is prepared as described in Section A except that the solution contains 350 mg/ml of a formula 1 base.

(D) A solution is prepared as described in Section A except that the solution contains 500 mg/ml of a formula 1 tartrate.

(E) A suspension is prepared by adding a finely ground formula 1 compound to carboxymethyl cellulose with thorough mixing so that the suspension contains 200 mg of the formula 1 base per ml of suspension.

I claim:

1. A compound of the formula

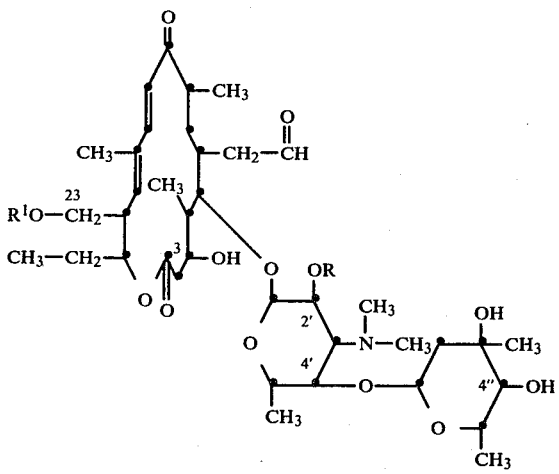

wherein R is selected from hydrogen, $C_1$–$C_5$-alkanoyl, $C_1$–$C_5$-alkanoyl having from one to three halo substituents, benzoyl, phenylacetyl or phenylpropionyl or benzoyl, phenylacetyl, or phenylpropionyl having on the phenyl ring from one to five halo or methyl or from one to two methoxyl, nitro or hydroxyl groups; and $R^1$ is an acyl group selected from:

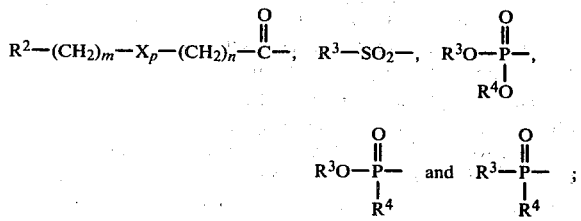

p is 0 or 1; m and n are integers from 0 to 4; $R^2$ is hydrogen, halo, $C_1$–$C_4$-alkyl, $C_3$–$C_8$-cycloalkyl, phenyl, $C_5$–$C_8$-cycloalkenyl, naphthyl, indenyl, tetralinyl, decalinyl, adamantyl, cinnoxacinyl, a monocyclic heterocyclic ring system comprising 3 to 8 atoms or a bicyclic heterocyclic ring system comprising 6 to 11 atoms, provided that at least 1 atom of the ring system is carbon and at least 1 atom of the ring system is a heteroatom selected from O, N, and S; and wherein $R^2$ and the connecting alkyl groups —$(CH_2)_m$— and —$(CH_2)_n$— are optionally substituted by one or two halo, methyl, ethyl, methoxy, amino, methylamino, dimethylamino, nitro, acetoxy, acetamido, azido, carbomethoxy, carboxamido, cyano, or hydroxyl groups, provided that, when the substituent is other than halo or alkyl, there can be no more than one substituent on any connecting —$CH_2$— group; X is O, S, —NH—, —N(CH$_3$)—, —C≡C—, —CH=CH—, —C(CH$_3$)=CH—, —CH=C(CH$_3$)— or —C(CH$_3$)=C(CH$_3$)—; $R^3$ and $R^4$ are $C_1$–$C_5$-alkyl, phenyl or benzyl or phenyl or benzyl having on the phenyl ring from one to five halo or methyl or from one to two methoxy, nitro or hydroxyl groups; and the acid addition salts thereof.

2. A compound of claim 1 wherein the acyl group is

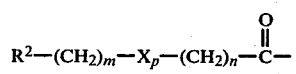

and the acid addition salts thereof.

3. A compound of claim 2 wherein $R^2$ is hydrogen or $C_1$–$C_4$-alkyl and the acid addition salts thereof.

4. A compound of claim 2 wherein p is 0 and the acid addition salts thereof.

5. A compound of claim 2, 3, or 4 wherein R is hydrogen and the acid addition salts thereof.

6. A compound of claim 2, 3, or 4 wherein R is $C_1$–$C_5$-alkanoyl and the acid addition salts thereof.

7. A compound of claim 2, 3, or 4 wherein R is benzoyl, phenylacetyl or phenylpropionyl and the acid addition salts thereof.

8. The compound of claim 3 wherein R and $R^1$ are acetyl and its acid addition salts.

9. The compound of claim 3 wherein R is hydrogen and $R^1$ is acetyl and its acid addition salts.

10. The compound of claim 3 wherein R and $R^1$ are propionyl and its acid addition salts.

11. The compound of claim 3 wherein R is hydrogen and $R^1$ is propionyl and its acid addition salts.

12. The compound of claim 3 wherein R is acetyl and $R^1$ is propionyl and its acid addition salts.

13. The compound of claim 3 wherein R is propionyl and $R^1$ is acetyl and its acid addition salts.

14. The compound of claim 3 wherein R is acetyl and $R^1$ is n-octanoyl and its acid addition salts.

15. The compound of claim 3 wherein R is acetyl and $R^1$ is pivaloyl and its acid addition salts.

16. The compound of claim 3 wherein R is acetyl and $R^1$ is methoxycarbonyl and its acid addition salts.

17. The compound of claim 3 wherein R is hydrogen and $R^1$ is methoxycarbonyl and its acid addition salts.

18. The compound of claim 3 wherein R is hydrogen and $R^1$ is [(8-amino-n-octyl)amino]carbonyl and its acid addition salts.

19. The compound of claim 3 wherein R is hydrogen and $R^1$ is [(3-hydroxy-n-propyl)amino]carbonyl and its acid addition salts.

20. A compound of claim 2 wherein $R^2$ is halo and the acid addition salts thereof.

21. The compound of claim 20 wherein R is acetyl and $R^1$ is trichloroacetyl and its acid addition salts.

22. A compound of claim 2 wherein $R^2$ is phenyl and the acid addition salts thereof.

23. The compound of claim 22 wherein R is acetyl and $R^1$ is phenylacetyl and its acid addition salts.

24. The compound of claim 22 wherein R is hydrogen and $R^1$ is phenylacetyl and its acid addition salts.

25. The compound of claim 22 wherein R is acetyl and $R^1$ is cinnamoyl and its acid addition salts.

26. The compound of claim 22 wherein R is acetyl and $R^1$ is phenoxyacetyl and its acid addition salts.

27. The compound of claim 22 wherein R is acetyl and $R^1$ is phenylpropionyl and its acid addition salts.

28. The compound of claim 22 wherein R is acetyl and $R^1$ is p-chlorophenylacetyl and its acid addition salts.

29. The compound of claim 22 wherein R is acetyl and $R^1$ is p-nitrophenylacetyl and its acid addition salts.

30. The compound of claim 22 wherein R is phenylacetyl and $R^1$ is phenylacetyl and its acid addition salts.

31. The compound of claim 22 wherein R is acetyl and $R^1$ is phenyl-n-valeryl and its acid addition salts.

32. The compound of claim 22 wherein R is acetyl and $R^1$ is 2,5-dimethoxyphenylacetyl and its acid addition salts.

33. The compound of claim 22 wherein R is acetyl and $R^1$ is benzylaminocarbonyl and its acid addition salts.

34. A compound of claim 2 wherein $R^2$ is adamantyl and the acid addition salts thereof.

35. The compound of claim 34 wherein R is acetyl and $R^1$ is adamantonoyl and its acid addition salts.

36. A compound of claim 2 wherein $R^2$ is a monocyclic heterocyclic ring system comprising 3 to 8 atoms and the acid addition salts thereof.

37. The compound of claim 36 wherein R is hydrogen and $R^1$ is (4-hydroxy-1-piperidinyl)carbonyl and its acid addition salts.

38. The compound of claim 36 wherein R is acetyl and $R^1$ is [[2-(4-morpholinyl)ethyl]amino]carbonyl and its acid addition salts.

39. The compound of claim 36 wherein R is acetyl and $R^1$ is 1H-imidazol-1-ylcarbonyl and its acid addition salts.

40. The compound of claim 36 wherein R is hydrogen and $R^1$ is 1H-imidazol-1-ylcarbonyl and its acid addition salts.

41. A method for controlling susceptible gram-positive infections which comprises administering to an infected or susceptible warm-blooded animal an effective amount of a composition comprising a compound of claim 1, 2, 3, 20, or 36 or a pharmaceutically acceptable acid addition salt thereof and a suitable pharmaceutical vehicle.

42. A composition for the control of susceptible gram-positive infections comprising an amount of a compound of claim 1, 2, 3, 20, or 36 or a pharmaceutically acceptable acid addition salt thereof which is effective against such infections and a suitable pharmaceutical vehicle.

* * * * *